(12) United States Patent
Han et al.

(10) Patent No.: US 11,428,690 B2
(45) Date of Patent: Aug. 30, 2022

(54) PORTABLE PLASMONIC SYSTEM FOR DISEASE DETECTION

(71) Applicant: University of Miami, Miami, FL (US)

(72) Inventors: Xu Han, Coral Gables, FL (US); Hossein Shokri Kojori, San Jose, CA (US); Roger M. LeBlanc, Key Biscayne, FL (US); Sung Jin Kim, Miami, FL (US)

(73) Assignee: University of Miami, Miami, FL (US)

( * ) Notice: Subject to any disclaimer, the term of this patent is extended or adjusted under 35 U.S.C. 154(b) by 423 days.

(21) Appl. No.: 15/883,851

(22) Filed: Jan. 30, 2018

(65) Prior Publication Data

US 2018/0217138 A1 Aug. 2, 2018

Related U.S. Application Data

(60) Provisional application No. 62/452,156, filed on Jan. 30, 2017.

(51) Int. Cl.
*G01N 33/543* (2006.01)
*H01L 31/108* (2006.01)
(Continued)

(52) U.S. Cl.
CPC ..... *G01N 33/54373* (2013.01); *G01N 21/554* (2013.01); *H01L 31/02161* (2013.01); *H01L 31/022408* (2013.01); *H01L 31/032* (2013.01); *H01L 31/09* (2013.01); *H01L 31/108* (2013.01); *H01L 31/165* (2013.01)

(58) Field of Classification Search
CPC ............ G01N 33/54373; G01N 21/554; H01L 31/09; H01L 31/165; H01L 31/032; H01L 31/02161; H01L 31/022408; H01L 31/108
See application file for complete search history.

(56) References Cited

U.S. PATENT DOCUMENTS 7,376,403 B1 * 5/2008 Wanke .................. H01L 29/205
257/19
7,420,225 B1 * 9/2008 Wanke .................. B82Y 10/00
257/184

(Continued)

OTHER PUBLICATIONS

Kojori et al "Plasmon Field Effect Transistor for Plasmon to Electric Conversion and Amplification" Nano Lett. 2016, 16, 250-254 (Year: 2015).*

(Continued)

*Primary Examiner* — Samuel P Siefke
*Assistant Examiner* — Quocan B Vo
(74) *Attorney, Agent, or Firm* — Christopher & Weisberg, P.A.

(57) ABSTRACT

A plasmonic photoconductor sensing platform is provided. The plasmonic photoconductor sensing platform includes an insulating substrate; a semiconducting film placed on top of the insulating substrate; two metal contacts placed at least in part on the semiconducting film to enforce an electric field; a plurality of plasmonic nanostructures deposited on the semiconducting film and physically separated from metal contacts; an insulating layer, the insulating electrically isolating the plasmonic nanostructures from semiconductor; at least one energy source; and at least one microfluidic channel disposed on the insulating layer.

16 Claims, 19 Drawing Sheets

(51) Int. Cl.
  *H01L 31/0224* (2006.01)
  *G01N 21/552* (2014.01)
  *H01L 31/0216* (2014.01)
  *H01L 31/032* (2006.01)
  *H01L 31/16* (2006.01)
  *H01L 31/09* (2006.01)

(56) References Cited

U.S. PATENT DOCUMENTS

| | | | | |
|---|---|---|---|---|
| 2003/0096302 | A1* | 5/2003 | Yguerabide | G01N 15/1468 435/7.1 |
| 2003/0143580 | A1* | 7/2003 | Straus | G01N 33/58 435/6.1 |
| 2003/0215865 | A1* | 11/2003 | Mayer | G01N 33/54373 435/6.19 |
| 2004/0005582 | A1* | 1/2004 | Shipwash | B01L 3/5027 435/6.19 |
| 2007/0257328 | A1* | 11/2007 | Gorrell | H01L 31/0224 257/428 |
| 2011/0005341 | A1* | 1/2011 | Neijzen | B29C 65/548 73/863.23 |
| 2013/0288916 | A1* | 10/2013 | Alexandre | C12Q 1/6876 506/9 |

OTHER PUBLICATIONS

Mayer et al. "Localized Surface Plasmon Resonance Sensors" Chem. Rev. 2011, 111, 6, 3828-3857 (Year: 2011).*

Ha Minh Hiep etal 2008 Jpn. J. Appl. Phys. 47 1337 (Year: 2008).*

Kojori et al "Supporting Information for Plasmon Field Effect Transistor for Plasmon to Electric Conversion and Amplification", Nano Lett. 2016, 16, 250-254 (Year: 2015).*

Brahmachari et al. "Performance analysis of a plasmonic sensor based on gold nanoparticle film in infrared light using the admittance loci method" Journal of Applied Physics 117, 083110 (2015); (Year: 2015).*

Hiep et al. "A Microfluidic Chip Based on Localized Surface Plasmon Resonance for Real-Time Monitoring of Antigen-Antibody Reactions" 2008 Jpn. J. Appl. Phys. 47 1337 (Year: 2008).*

Wang et al. "Functionalized MoS2 Nanosheet-Based Field-Effect Biosensor for Label-Free Sensitive Detection of Cancer Marker Proteins in Solution" small 2014, 10, No. 6, 1101-1105 (Year: 2014).*

Chen et al. "Silicon nanowire field-effect transistor-based biosensors for biomedical diagnosis and cellular recording investigation" Nano Today (2011) 6, 131-154 (Year: 2011).*

Hwang et al. "Ultrasensitive PbS quantum-dot-sensitized InGaZnO hybrid photoinverter for near-infrared detection and imaging with high photogain" NPG Asia Mater 8, e233 (2016) (Year: 2016).*

Shen et al. "Silicon nanowire field-effect-transistor based biosensors: From sensitive to ultra-sensitive" Biosensors and Bioelectronics vol. 60, Oct. 15, 2014, pp. 101-111 (Year: 2014).*

Zhang et al. "Silicon nanowire biosensor for highly sensitive and rapid detection of Dengue virus" Sensors and Actuators B 146 (2010) 138-144 (Year: 2010).*

* cited by examiner

PORTABLE PLASMONIC SYSTEM FOR DISEASE DETECTION

CROSS-REFERENCE TO RELATED APPLICATION

This application is related to and claims priority to U.S. Provisional Patent Application Ser. No. 62/452,156, filed Jan. 30, 2017, entitled PORTABLE PLASMONIC SYSTEM FOR DISEASE DETECTION, the entirety of which is incorporated herein by reference.

STATEMENT REGARDING FEDERALLY SPONSORED RESEARCH OR DEVELOPMENT

This invention was made with Government support under contract number 1355317 awarded by the National Science Foundation.

TECHNICAL FIELD

The present invention relates to a method, a device, and a system for detecting a binding event between a ligand and ligand-binding agent, and in particular, to a portable biosensing system for measuring biomarkers to indicate the corresponding and ongoing biological conditions. This invention uses a plasmonic field effect transistor and a plasmonic photoconductor platform in a portable biosensing system that directly detects plasmonic energy to an electrical signal. This system includes a lock-in amplifier that may convert the plasmonic energy into an electrical signal. In addition, the microfluidic control unit which is integrated with electrical detection unit may manage the delivery of biomaterials on the sensing area.

BACKGROUND

Advanced development in nanotechnology for the exploitation of localized surface plasmon resonances ("LSPR") in nanophotonics as well as biotechnology has occurred in recent decades. The mechanism of LSPR involves the hot electron transfer in response to a specific energy being absorbed. This occurs when the plasmonic nanomaterials, mainly metal, are placed in an electromagnetic field where the size of the nanomaterials is much smaller than the wavelength of the incident photons. The specific energy of this incoming light can induce a resonance of electrons as illustrated in FIG. 1. Thereafter, the induced hot electron has enough energy that it can overcome the Schottky barrier, which is formed at the boundary between metal and a semiconductor or non-plasmonically absorbed electrons can also move to a semiconductor part if the metal-semiconductor forms an Ohmic junction.

FIG. 2 illustrates the Schottky barrier which is denoted as $\varphi_B$ for an n-type semiconductor, demonstrating the difference between the interfacial conduction band edge $E_C$ and Fermi level $E_F$. $E_v$ refers to the valence band in FIG. 2. FIG. 3 also illustrates the Schottky barrier similar to FIG. 2, where the thin insulating wall will not affect the Schottky barrier. In addition, the induced hot electron can penetrate the thin insulating wall due to the quantum tunneling effect.

After passing through the Schottky barrier, the induced hot electron will be migrated into the semiconductor. This process demonstrates different plasmonic absorption depending upon size, material, and the surrounding refractive index of the plasmonic nanomaterials. Therefore, LSPR based biosensor is sensitive towards the molecule bounded to plasmonic nanomaterials as a result of binding induced altered surrounding refractive index.

Since the discovery of this label-free LSPR based biosensor, it has demonstrated a great potential to serve as a point-of-care testing ("POCT") device, where the medical diagnostic testing is in proximity to the patient's location.

SUMMARY

This present invention can be used many applications. For example, biomarker or biological marker, which can rapidly and correctly indicate the corresponding ongoing biological conditions, has begun to stand out as a competitor to other developed strategies. Therefore, the successful sensing of different biomarkers by the LSPR based biosensor can help improve the diagnosis of cancers and many other diseases. However, the drawbacks of existing LSPR based biosensor include: 1) complicated structure, 2) indirect detection of the plasmonic energy, 3) indirect illumination of the incident energy such as light, 4) low sensitivity, and/or 5) do not function well with human blood. To this end, In instant invention solves at least some of the problems with existing systems by providing a portable disease detecting device and system, which provides real-time measurement and multiplexing capability.

In one or more embodiments, the present invention provides a plasmonic field effect transistor plasmonic photoconductor sensing platform, a portable biosensing system, and method for detecting a binding event between a ligand and ligand-binding agent. In view of the foregoing background, one application of the present invention is to help improve the diagnosis of cancers and many other diseases.

In one or more embodiments, a plasmonic field effect transistor based sensing platform is presented, as illustrated in FIG. 19. The plasmonic photoconductor sensing platform may preferably comprise: transparent wide bandgap semiconductor; metal contacts for the gate, drain and source, multiple metal nanostructures on top of a semiconductor layer; transparent conducting film for the gate; drain and source; multiple metal nanostructures on the top semiconductor layer; an insulating layer; at least one back illumination light source; and at least one microfluidic channel. The microfluidic channel is aligned to the plasmonic field effect transistor so the metal nanostructures are in direct contact with the fluidic channel.

The light source provides back side illumination to the metal nanostructures. This light illumination directly illuminates the plasmonic nanostructure on the plasmon field effect transistor without any obstruction by the liquid samples in the fluidic channel. The contact between the metal nanostructures and the fluidic channel, and the contact between the metal nanostructures and the illumination are opposite. The metal nanostructures can affect the photocurrent in the semiconductor layer depending on the absorption of incident energy, and metal nanostructures are electrically isolated from other parts by the insulating layer.

A gate electrode and insulating layer removed plasmon field effect transistor (i.e. plasmonic photoconductor) sensing platform is presented. The elimination of gate and the insulating layer can offer a simpler device structure and less device fabrication costs. The plasmonic photoconductor sensing platform, as illustrated in one or more figures herein, may comprise an insulating substrate 06, a semiconducting film 03 on the substrate 06, two metal contacts 08, an insulating layer 09, multiple plasmonic nanostructures 04, at least one back illumination light source 07, and at least one microfluidic channel 11. The plasmonic photoconductor sensing platform may also further include a thin (<4 nm) insulating wall 05 between the semiconducting film 03 and multiple plasmonic nanostructures 04 wherein the semiconducting film 03 and multiple plasmonic nanostructures 04 are in direct contact with the thin insulating wall 05, respectively. Plasmon induced electrons 12 can penetrate the thin insulating wall 05 because of quantum tunneling effect. The microfluidic channel 11 is aligned to the plasmonic photoconductor sensing platform so that the plasmonic nanostructures are in direct contact with the fluidic channel. The light source 07 provides back side illumination to the multiple plasmonic nanostructures. The contact between multiple plasmonic nanostructures and the fluidic channel and the contact between multiple plasmonic nanostructures and the illumination are opposite. Multiple plasmonic nanostructures 04 can affect the photocurrent in the semiconducting film 03 depending on the absorption of incident energy 07, and multiple plasmonic nanostructures 04 are electrically isolated from other parts by the insulating layer 09.

The portable biosensing system consists of one of the previously described plasmonic sensing platforms (plasmonic field effect transistor or the plasmonic photoconductor sensing platform) in this invention. The portable biosensing system may further include: at least one direct current power source, which is employed to provide the voltage biases; at least one lock-in amplifier circuit (or equivalent digital signal process after analog-to-digital conversion of the detected electrical signal), which uses the current from the plasmonic sensing platforms to remove the background noise and direct current; at least one resistor, which is used to transfer the generated photocurrent from the plasmonic field effect transistor or the plasmonic photoconductor sensing platform to the voltage unit signal; at least one serial or parallel communication unit; at least a signal processing software to read and analyze the sensor detection data where the signal processing software, in one or more embodiments, is stored in a memory of at least a host device such as a computer and a smart phone to demonstrate the result; and at least one external light source at least one narrowband optical filter for the light source that provides broadband spectrum.

A functionalization method of the plasmonic field effect transistor and the plasmonic photoconductor sensing platform is presented. Initially, the metal nanostructures or the plasmonic nanostructures 04 may be exposed and incubated with a linker 14. The linker 14 may be at least one of an oligopeptide linker or a hydrocarbon molecule. The linker 14 molecule may be one or more thiol groups terminated or disulfide groups terminated, and the other end of the linker 14 molecule may be at least one of the group consisting of an N-hydroxysuccinamide (NHS) ester, an aldehyde, a maleimide, an epoxide, a carboxyl group, an amine group, and a hydroxyl group. After the linker incubation, the unreacted linker may be washed off by phosphate-buffered saline (PBS) buffer. Secondly, the plasmonic nanostructures 04 with the attached linker 14 may be incubated with the ligand 16. The ligand 16 may be at least one from the group consisting of a peptide, a protein, a oligonucleotide, and a virus. After incubation, the unreacted ligand 16 may be washed off by a phosphate-buffered saline (PBS) buffer. Thirdly, the plasmonic nanostructures 04, with the attached linker 14 and ligand 16, may be incubated with passivation molecules 15. The passivation method may include at least one from the group consisting of detergent blockers, such as Tween-20 and Triton X-100, protein blockers, such as bovine serum albumin, casein, fish gelatin, and whole sera, and polymer based blockers, such as polyethylene glycol, polyvinyl alcohol, polyvinylpyrrolidone, polyacrylic acid, polyacrylic maleic acid.

In addition, if the linker 14 contains a polyethylene glycol (PEG) moiety, it may also be one the passivation methods. Finally, the plasmonic field effect transistor and the plasmonic photoconductor sensing platform may be used to detect different ligand-binding agent to show specific binding towards the ligand used in the functionalization method. The result of the existence or the concentration of the ligand binding agent may be directly from at least one portable biosensing system. The result of the existence or the concentration of the ligand binding agent may further include the result comparison of at least two portable biosensing systems. One portable biosensing system may work as a working device, where the metal nanostructures or the plasmonic nanostructures may be functionalized by the ligand which shows specific binding towards the ligand binding agent, using the functionalization method. The other portable biosensing system may work as a reference device, where the metal nanostructures or the plasmonic nanostructures are not functionalized by the ligand which shows specific binding towards the ligand binding agent. But the metal nanostructures or the plasmonic nanostructures in the reference and the metal nanostructures or the plasmonic nanostructures are functionalized by the same linker which is utilized in the working the metal nanostructures or the plasmonic nanostructures system, using the claimed functionalization method. Both portable biosensing systems may use the same passivation method.

One application of the present invention, including the plasmonic field effect transistor, the plasmonic photoconductor sensing platform, and the portable biosensing system, may be to detect different biomarkers in either blood, sweat, or spit. The biomarker is a substance in an organism and its presence is indicative of some phenomenon, including diseases and cancers. The present invention may achieve real-time multiplexing measurements. For example, cardiac troponin I, cardiac troponin T, myoglobin, an isoenzyme of creatine kinase are considered as the protein biomarker for heart disease. The antibody of each protein biomarker can be the ligand 16 which are attached to the metal nanostructures or the plasmonic nanostructures 04 using the claimed functionalization method. The functionalized plasmonic field effect transistor, or plasmonic photoconductor sensing platform, or portable biosensing system can be used to detect the existence or the concentration of biomarker in human blood in a real-time multiplexing fashion, so that the present invention, including the plasmonic field effect transistor, the plasmonic photoconductor sensing platform, and the portable biosensing system, can help improve the diagnosis of heart diseases.

According to one aspect of the disclosure, a plasmonic photoconductor sensing platform is provided. The plasmonic photoconductor sensing platform includes an insulating substrate, a semiconducting film placed on top of the insulating substrate, two metal contacts placed at least in part on the semiconducting film to enforce electric field, multiple plasmonic nanostructures deposited on the semiconducting film and physically separated from metal contacts, an insulating layer which electrically isolate the plasmonic nanostructures from semiconductor, at least one energy source, and at least one microfluidic channel anchored on the insulating layer.

In one embodiment of this aspect, the semiconducting film operates as an electron path. The multiple plasmonic nanostructures, which are not in direct contact with the metal contacts, are configured to absorb photons provided by the light source and generate plasmonic hot electrons to affect the photocurrent in the semiconducting film. The multiple plasmonic nanostructures and the semiconducting film create a Schottky Junction that allows only plasmonic hot electron transfer from the multiple plasmonic nanostructures to the semiconducting film. The light source can provide back side illumination, and may be placed at least one of the locations which are below the substrate, partially or fully embedded inside the substrate, and on top of the substrate. The light source may be further modulated with a narrow optical or polarizer filer or a switching electric circuit, so as to provide energy with different wavelength number. The microfluidic channel, wherein the inlet of the microfluidic channel may further include at least one plasma separation membrane, is aligned to the plasmonic photoconductor sensing platform so that the plasmonic nanostructures are in direct contact with the fluidic channel. The plasmonic photoconductor sensing platform may further include a thin insulating wall between the semiconducting film and multiple plasmonic nanostructures. The semiconducting film and multiple plasmonic nanostructures are in direct contact with the thin insulating wall, respectively. The light source can be placed at one of below the thin insulating wall, partially or fully embedded inside the thin insulating wall, and on top of the thin insulating wall.

According to one embodiment of this aspect, the insulating substrate can be either transparent in or opaque in visible spectrum. According to one embodiment of this aspect, the semiconducting film may have an absorption spectrum that is not overlapped with the plasmonic resonance spectrum; metal contacts for voltage bias; multiple plasmonic nanostructures is at least one of gold, silver, aluminum, copper, tungsten, doped metal oxide and the shape of multiple plasmonic nanostructures is at least one of sphere, semi-sphere, cylinder, cube, cone, pyramid or random structure; the light source(s) such as light emitting device (LEDs) or laser; the microfluidic channel is at least one of polydimethylsiloxane (PDMS) molding solution, polyethylene terephthalate (PET), and poly(methyl methacrylate) (PMMA). The thin insulating wall is one of SiO2 and HfO.

According to one aspect of the disclosure, the portable biosensing system designed for real-time parallel multiplexing detection of a ligand-binding agent to the ligand is provided. The portable biosensing system includes the plasmonic photoconductor sensing platform, at least one source meter, which is employed to provide the voltage biases, at least one lock-in amplifier circuit or signal processing software, which is connected to the plasmonic field effect transistor or the plasmonic photoconductor sensing platform to remove the background noise, at least one resistor, which is used to transfer the generated photocurrent from the plasmonic field effect transistor or the plasmonic photoconductor sensing platform to the voltage unit signal, at least one serial or parallel communication method; at least a signal processing software to read and analyze the sensor detection data, at least a host device such as the computer and the smart phone to demonstrate the result; at least one external light source, and at least one narrowband optical filter at correspondence light emitting diode frequencies.

According to one aspect of the disclosure, methods for functionalizing the portable biosensing system are provided where the methods include: means for functionalizing the plasmonic nanostructures; means for eliminating non-specific binding; means for detecting a ligand-binding agent attached to the ligand; means for functionalizing plasmonic nanostructures may include the linker covalently or non-covalently attachment to the plasmonic nanostructures via an oligopeptide linker or a hydrocarbon linker; ligand covalently or non-covalently attachment to the linker on the plasmonic nanostructures.

In one embodiment of this aspect, the hydrocarbon linker molecule is thiol groups terminated or disulfide, and the other end of the linker molecule is at least one of N-hydroxysuccinamide (NHS) ester, aldehyde, maleimide, epoxide, a carboxyl group, an amine group, hydroxyl group; ligand is at least one of the peptide, protein, oligonucleotide, virus. The ligand-binding agent shows specific binding towards the ligand used, and the binding of ligand-binding agent to the ligand is effective to measurably change the photocurrent in the electron path. Means for eliminating non-specific binding includes one of detergent blockers, such as Tween-20 and Triton X-100, and protein blockers, such as bovine serum albumin, casein, fish gelatin, and whole sera, and polymer based blockers, such as polyethylene glycol, polyvinyl alcohol, polyvinylpyrrolidone, polyacrylic acid, polyacrylic maleic acid. In addition, if the linker contains polyethylene glycol (PEG) moiety, it is also one of the passivation methods. The detecting means may include circuit means for removing interferences signals, circuit means for measuring photocurrent across the electron path, and may further include circuit means for removing the reference plasmonic photoconductor sensing platform signal from the working plasmonic photoconductor sensing platform signal, whereby the plasmonic nanostructures in the reference plasmonic photoconductor sensing platform is not functionalized by the ligand which shows specific binding towards the ligand binding agent, but the plasmonic nanostructures is functionalized by the linker used in the working plasmonic photoconductor sensing platform.

According to one aspect of the disclosure, one application of the portable biosensing system is to detect different biomarkers in human or animal fluids such as blood, sweat, and spit. The biomarker is a substance in an organism whose presence is indicative of some phenomenon, including diseases and cancers.

According to one aspect of the disclosure, a plasmon field effect transistor is integrated into the same system as discussed herein.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

The present invention provides a plasmonic field effect transistor, plasmonic photoconductor sensing platform, portable biosensing system, and method for detecting a binding event between a ligand and ligand-binding agent, and in particular, to a biosensing system for measuring biomarkers to indicate the corresponding and ongoing biological conditions.

Figure 4:
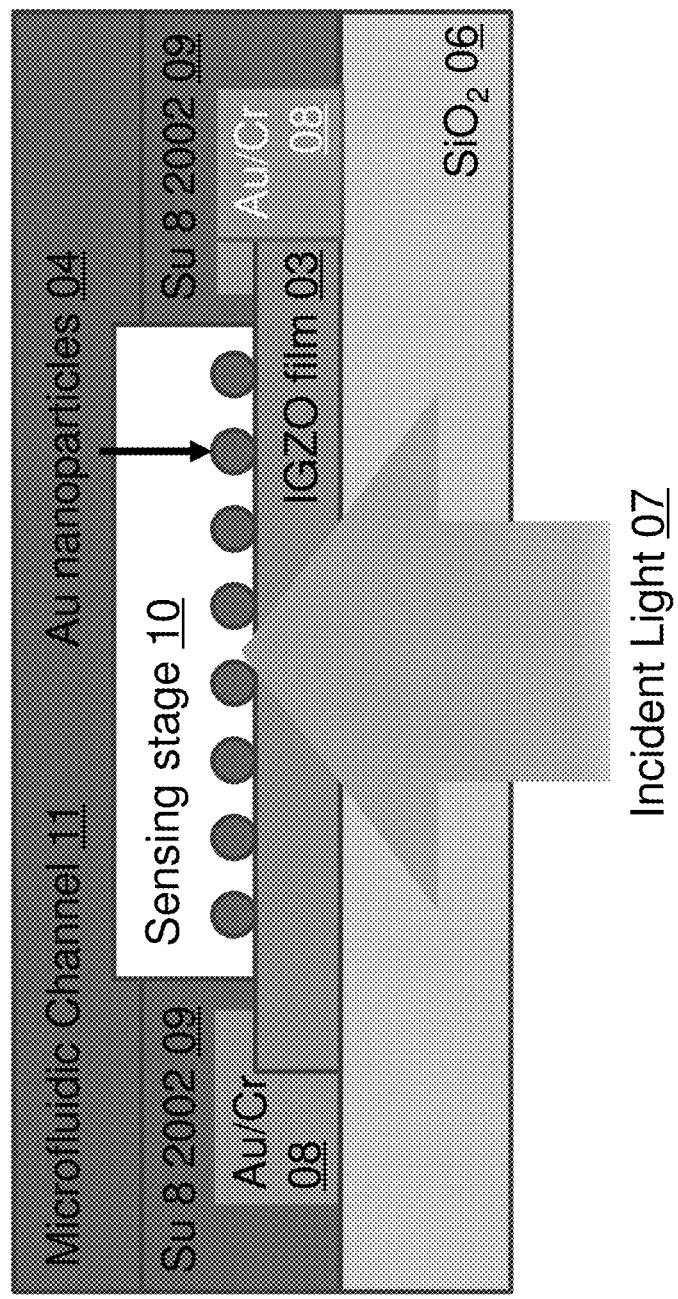
FIG. 4 is a diagram of one example embodiment of a plasmonic photoconductor sensing platform.
Figure 7:
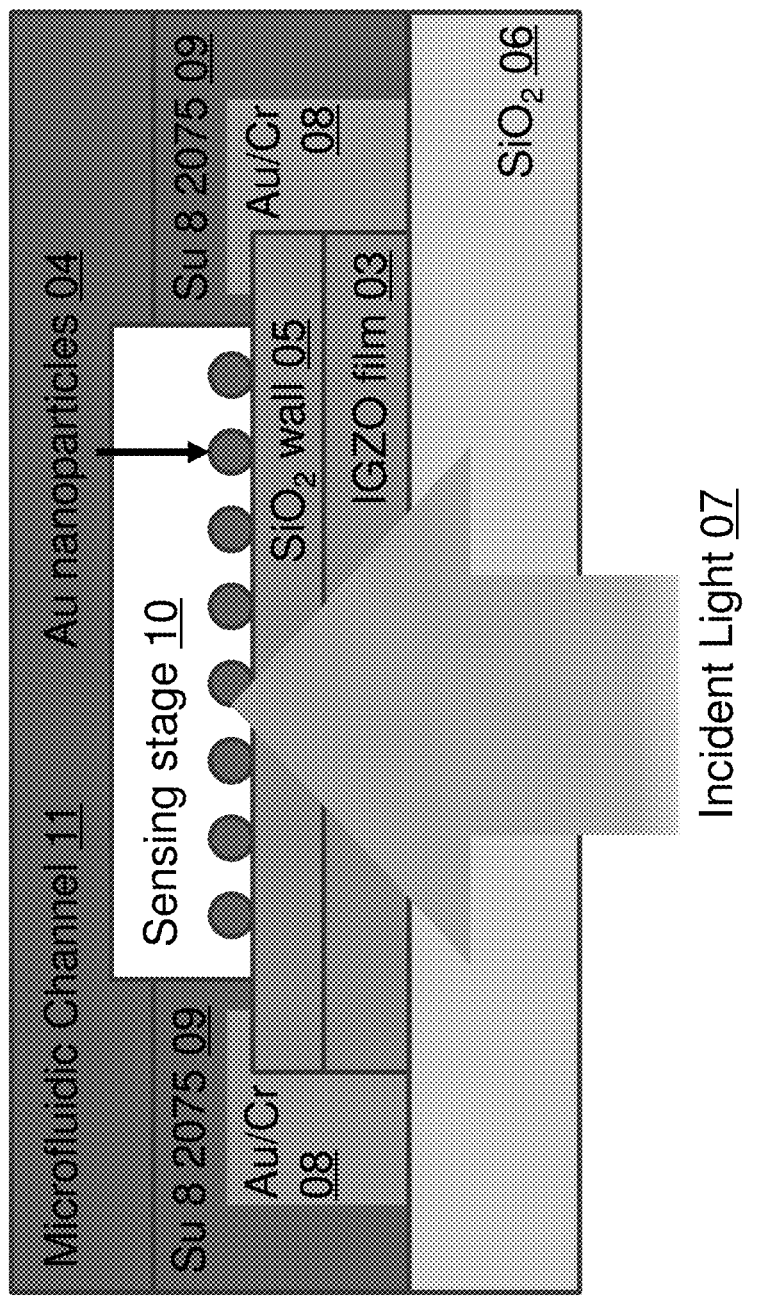
FIG. 7 is a diagram of one example embodiment of a plasmonic photoconductor sensing platform.

Referring to FIGS. 4 and 7, these figures demonstrate an example embodiment of the plasmonic photoconductor sensing platform in accordance with the principles of the present invention. The plasmonic photoconductor sensing platform 01 include a semiconducting film 03 which is an n-type InGaZnO (IGZO) film. The IGZO film is a wide bandgap semiconductor channel so as to avoid the spectral overlap between the plasmonic absorption of the metal nanostructure and the absorption of the semiconducting layer. If the device satisfies the same spectral overlap condition. The semiconducting film 03 is not limited to IGZO, and may alternatively utilize other transparent materials $TiO_2$, ZnO, GaN or semiconducting organic compounds. In this case the, the plasmonic nanostructures may have their plasmonic resonance at the near infrared (i.e. 1000 nm-2000 nm), the semiconductor layer can be replaced with a Si or other opaque semiconductor materials. The thickness of the semiconducting film 03 may be from 1 nm to 90000 nm, depending on the design requirement.

The plasmonic photoconductor sensing platform may further include an insulating substrate 06. The insulating substrate 06 may be at least one of the group consisting of $SiO_2$, Si, Silica, Polyethylene terephthalate (PET), poly (methyl methacrylate) (PMMA), acrylic materials, quartz, glass, printed circuit board or other transparent polymer materials and opaque insulating materials. The semiconducting film 03 may be placed on the substrate 06.

The plasmonic photoconductor sensing platform may also include a thin insulating wall 05 which is placed on the semiconducting film 03. The thin insulating wall 05 may be at least one of the group consisting of $SiO_2$, HfO, parylene, $Al_2O_3$ or another. The thickness of the thin insulating wall 05 may be between 0.1 nm to 5 nm. Electrons may be able to penetrate this thin insulating wall 05 because of quantum tunneling effect.

The plasmonic photoconductor sensing platform may further include two metal contacts 08. Metal contacts 08 may be used to apply the voltage bias to the device. Metal contacts 08 may be disposed on the insulating substrate 06 and at least in part contact with the semiconducting film 03.

The plasmonic photoconductor sensing platform 01 may further include one or more plasmonic nanostructures 04 placed on the semiconducting film 03 or the thin insulating wall 05. The plasmonic nanostructures 04 are electrically isolated from the metal contacts 08. The nanostructures 04 is at least one of gold, silver, aluminum, copper, tungsten, or doped metal oxide. The shape of the nanostructures 04 is at least one of the sphere, semi-sphere, cylinder, cube, and rod, start, sea urchin, or random shapes. The nanostructures 04 may exhibit plasmonic effects, such as surface plasmon resonance or localized surface plasmon resonance. For example, the nanostructures 04 may be gold nanoparticle that presents localized surface plasmon resonance in visible color. If the gold nanoparticle is surrounded with other molecules or materials, the absorption peak will increase at the measured wavelength as a result of altered refractive index.

Figure 1:
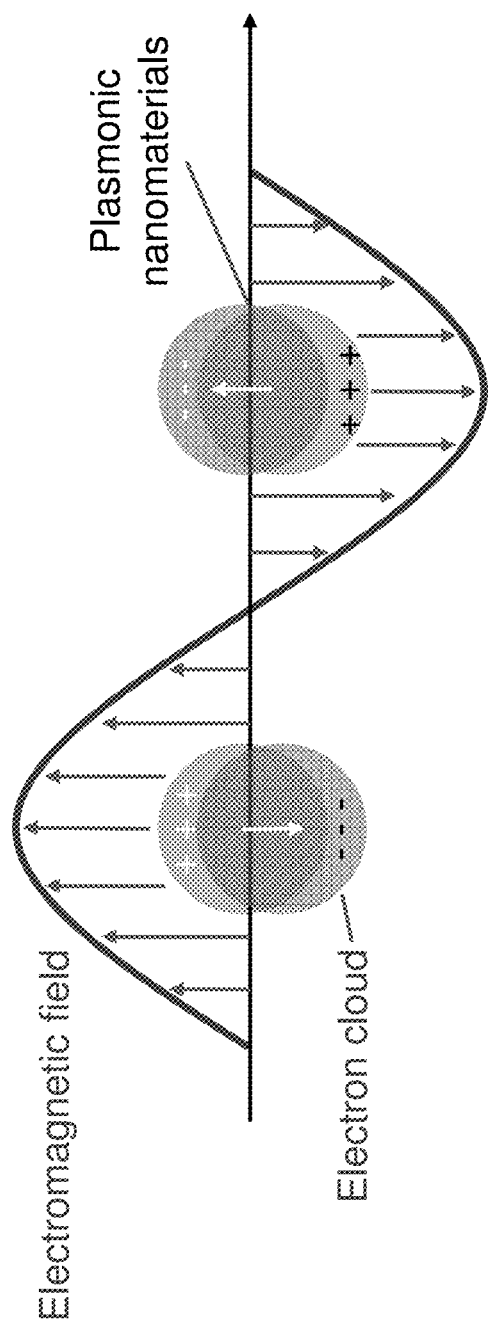
FIG. 1 is a diagram of an induced electron oscillation by the electromagnetic field.
Figure 2:
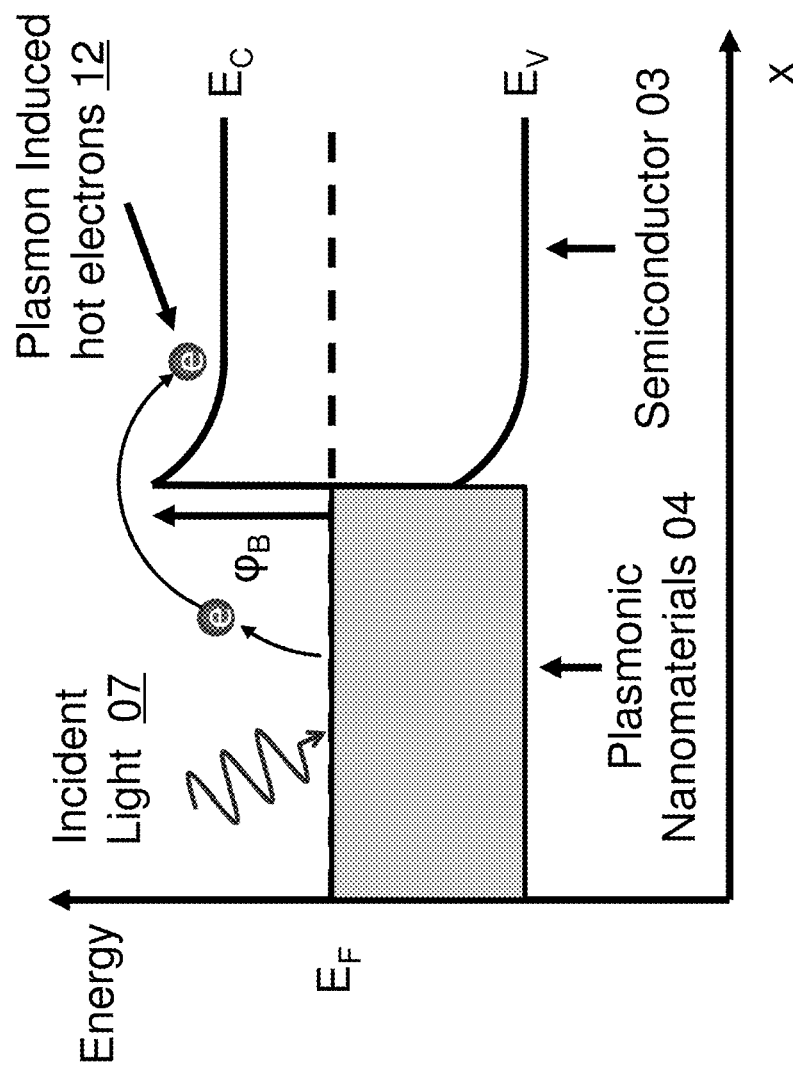
FIG. 2 is a diagram of induced hot electron migration at Schottky junction.
Figure 3:
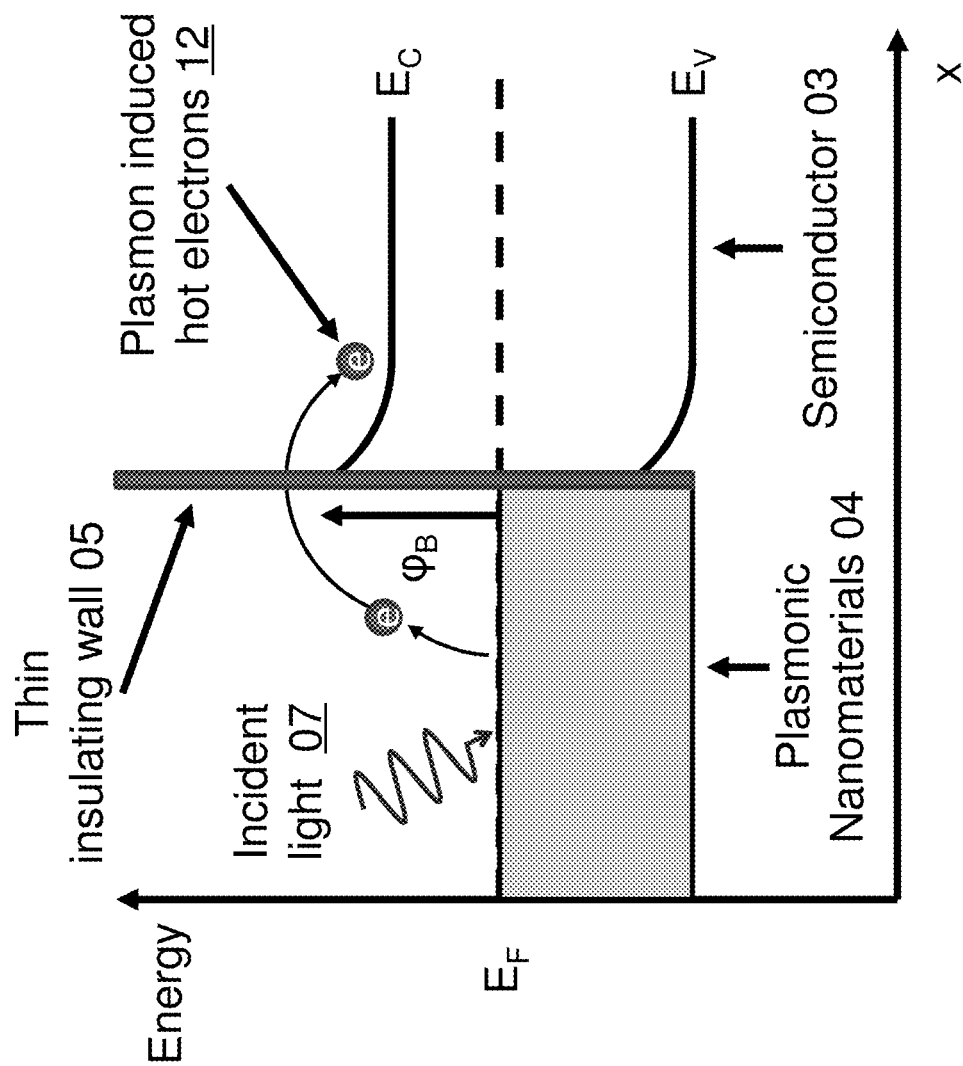
FIG. 3 is a diagram of induced hot electron penetrate the thin insulating wall and migrate into semiconductor at Schottky junction.

The nanostructures 04 and the semiconducting film 03 may form a Schottky junction (a potential energy barrier denoted by $\varphi_B$) at the metal-semiconductor junction or Ohmic junction. FIG. 2 illustrates the plasmon induced hot electron migration at Schottky Junction 13 of the plasmonic photoconductor sensing platform 01, whereby the plasmon induced hot electrons 12 are generated due to the absorption of the incident light 07 by the plasmonic nanomaterials 04. Induced hot electrons 12 with the energy that is higher than the Schottky barrier can migrate from the plasmonic nanomaterials 04 to the semiconducting film 03, leading to the increased photocurrent in electron path. FIG. 3 also illustrates the plasmon induced hot electron migration at Schottky Junction 13 of the plasmonic photoconductor sensing platform 01, whereby a thin insulating wall 05 (<4 nm) was added between the plasmonic nanomaterials 04 and the semiconducting film 03. Due to the quantum tunneling effect, electrons can penetrate this insulating layer 05. In the case of Ohmic junction, the hot electrons generated by plasmon resonance and non-plasmonic energy absorption. And the plasmonic response can be detected by using the same method used for Schottky junction based device.

The sensing stage 10 in the plasmonic photoconductor sensing platform is the semiconducting film 03 where placed the nanostructures 04 or the thin insulating wall 05 where placed the plasmonic nanomaterials 04. The size of the sensing stage may range from 1 μm to 10000 μm.

The plasmonic photoconductor sensing platform may further include an insulating layer 09. The insulating layer 09 electrically isolate the sensing stage 10 from other areas.

The plasmonic photoconductor sensing platform may further include one or more microfluidic channel 11. The microfluidic channel 11 may be at least one of the group consisting of polydimethylsiloxane molding solution (PDMS), polyethylene terephthalate (PET), and poly (methyl methacrylate) (PMMA). The dimensions of microfluidic channel 11 may be selected according to the size of the plasmonic photoconductor sensing platform. The size of the plasmonic photoconductor sensing platform may range from 1 mm to 30 cm in its diagonal direction or diameter.

The injection may be done using a commercial needle, making this device more suitable for mass production and industrial use.

The inlet of the microfluidic channel may further include at least one plasma separation membrane. The microfluidic channel 11 mold may be patterned on top of the plasmonic photoconductor sensing platform. The following process may used to fabricate the microfluidic channel:

1. Prepare Polydimethylsiloxane (PDMS) molding solution
   Mix Sylgard 184 Base with Curing Agent at a ratio of 10 (base, 25 g) to 1 (curing agent, 2.5 g) by weight for 15 mins.
2. Remove all bubble from molding solution (PDMS)
   Put the PDMS in Vacuum Chamber (Vacuum 25 psi for 15 mins twice)
3. Molding
   a) Put a patterned wafer in a petri dish.
   b) Pour PDMS on the wafer.
   c) Remove bubble again by using a pipette (without vacuum chamber).
   d) Put the Petri dish on an optical table, and wait for a day
4. Remove mold and Cut the patterned PDMS
5. Attach microfluidic PDMS to the device
   a) Expose the device to ozone plasmon for 30 mins
   b) Put the PDMS on the device by using Mask Aligner. The microfluidic channel is aligned onto the plasmonic photoconductor sensing platform 01, so that the sensing stage 10 can be exposed to the injected samples in the microfluidic channel 11.

The light source 07 may be at least one of the group consisting of a light emitting device (LEDs), a laser and a light bulb. Those light sources may provide wavelengths ranging at least from 350 nm to 2500 nm. The spectral range may depend on the light source properties. The light source 07 may provide back side illumination, and may be placed at least one of the locations which are below the substrate, partially or fully embedded in the substrate, and on top of the substrate. The light source 07 may be further modified with a narrow optical filter or polarizer. To use lock-in method to detect the plasmonically generated signal, the light may be modulated by an electric circuit or mechanical chopping.

FIG. 4 illustrates one representation of the plasmonic photoconductor sensing platform. In particular, a) the insulating substrate 06 is a transparent $SiO_2$ substrate; b) the semiconducting film 03 is a n-type IGZO film with a thickness of 50 nm; c) plasmonic nanomaterials 04 are gold nanoparticles; d) the insulating layer 09 is Su 8 2002 which electrically isolate the sensing stage 10 from other areas; e) the microfluidic channel is polydimethylsiloxane molding solution (PDMS), and aligned onto the plasmonic photoconductor sensing platform so as to expose the sensing stage 10 to the injected samples in the microfluidic channel 11; f) a Light Emitting Device (LED) 07 with a narrow bandwidth optical filter is placed below the $SiO_2$ substrate.

Figure 5:
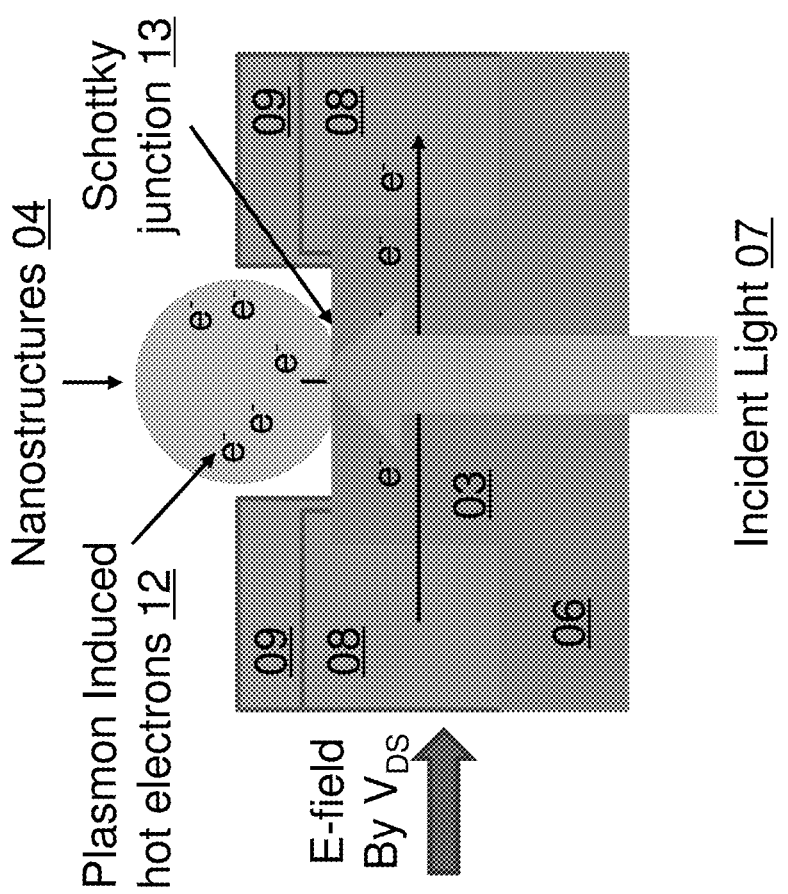
FIG. 5 is a diagram of an induced hot electron migration at Schottky junction.
Figure 6:
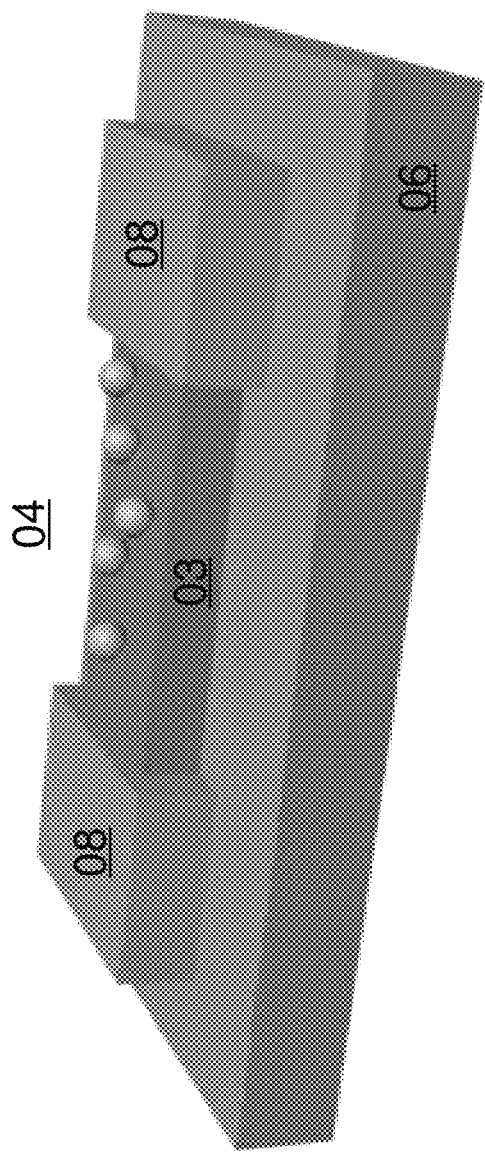
FIG. 6 is a perspective view of the plasmonic photoconductor sensing platform.

FIG. 5 illustrates that the plasmon induced hot electrons 12 migrate from gold nanoparticles 04 to IGZO film 03, resulting in increased photocurrent in electron path. FIG. 6 illustrates the perspective view of the plasmonic photoconductor sensing platform, where one or more plasmonic photoconductor sensing platform 01 can be placed on the insulating substrate 06.

FIG. 7 is similar to FIG. 4, illustrating another embodiment of the plasmonic photoconductor sensing platform. In particular, a) the substrate 06 is a transparent $SiO_2$ substrate; b) the semiconducting film 03 is a n-type IGZO film with a thickness of 50 nm; c) the thin insulating film 05 is $SiO_2$ with the thickness of 2 nm; d) plasmonic nanomaterials 04 are gold nanoparticles; e) the insulating layer 09 is Su 8 2002 which electrically isolate the sensing stage 10 from other areas; f) the microfluidic channel is polydimethylsiloxane molding solution (PDMS), and aligned onto the plasmonic photoconductor sensing platform so as to expose the sensing platform 10 to the injected samples in the microfluidic channel 11; g) a Light Emitting Device (LED) 07 with a narrow bandwidth optical filter is placed below the $SiO_2$ substrate.

Figure 8:
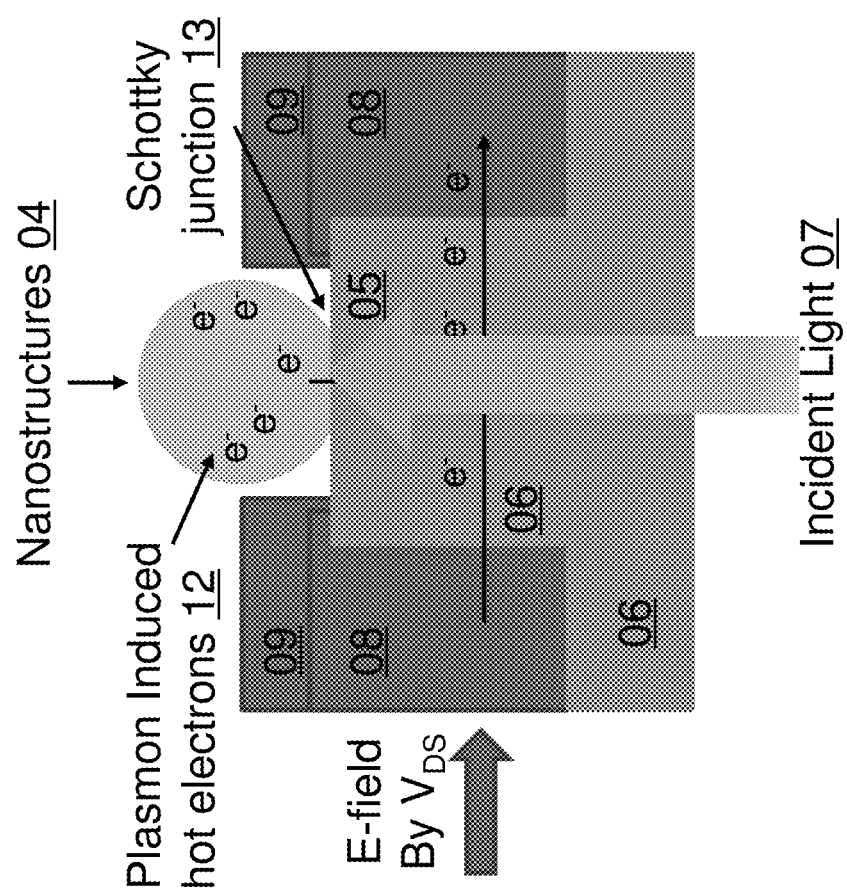
FIG. 8 is a diagram of an induced hot electron penetrate the thin insulating wall and migrate into the semiconductor at Schottky junction.
Figure 9:
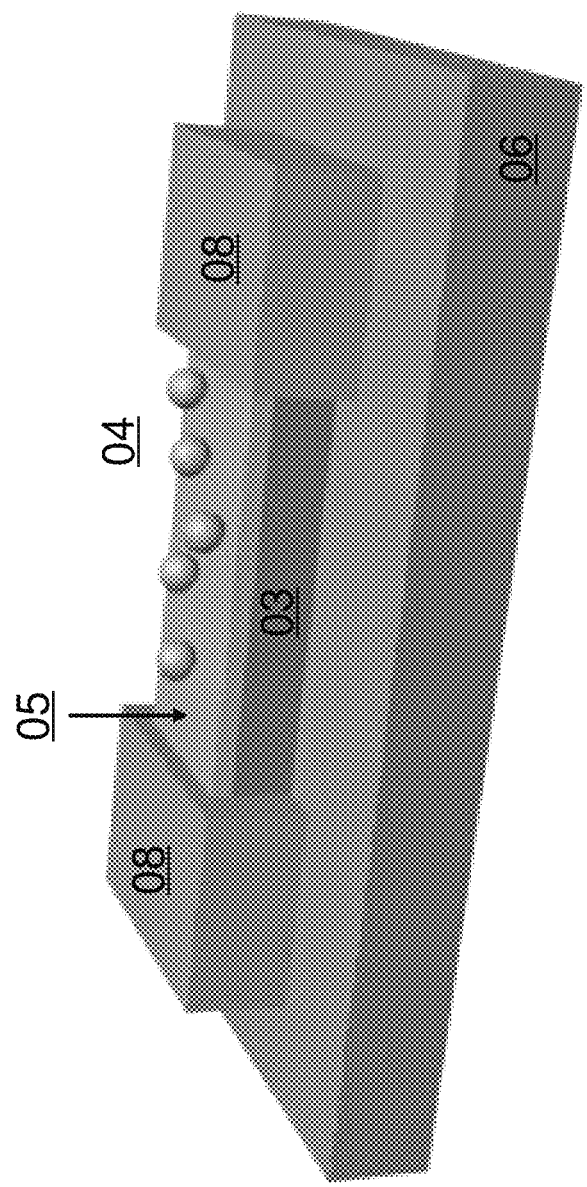
FIG. 9 is a perspective view of the plasmonic photoconductor sensing platform.

FIG. 8 illustrates that the plasmon induced hot electrons 12 migrate from gold nanoparticles 04 to IGZO film 03, resulting in increased photocurrent in electron path. The plasmon induced hot electrons 12 can penetrate the 2 nm $SiO_2$ film 05 because of quantum tunneling effect. FIG. 9 illustrate the perspective view of the plasmonic photoconductor sensing platform, where one or more the plasmonic photoconductor sensing platform can be placed on the insulating substrate 06.

Figure 10:
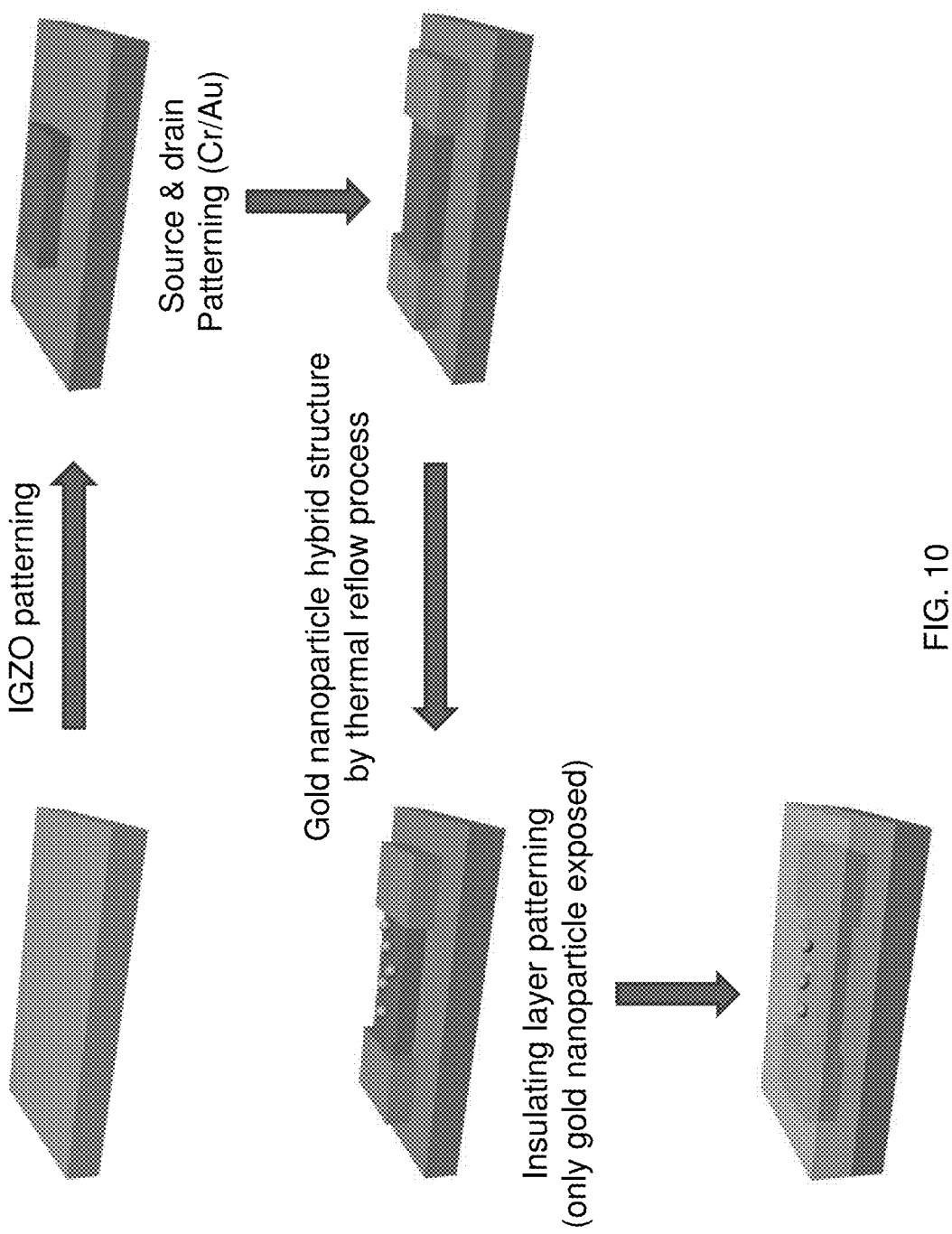
FIG. 10 is a fabrication flow diagram of the plasmonic photoconductor sensing platform.

FIG. 10 illustrates the fabrication process flow of the plasmonic photoconductor sensing platform. Initially, a silica insulating substrate 06 was rinsed in acetone, methanol, and DI water for 15 min, respectively. A 50 nm n-type IGZO film 03 was then deposited onto the channel layer, using an RF magnetron sputtering and an IGZO target (2 inch size and 99.99% purity) with 90 Watts of RF power under 6.2 mTorr Ar ambient at a temperature of 25° C. The substrate was rotated to achieve thickness uniformity with 0.8 nm/min deposition rate. A typical photolithography process and a wet etching process were utilized for the channel isolation, and the n-type IGZO film 03 was patterned using diluted HCl solution (2%).

To create a metal contact between electrodes and the n-type IGZO film 03, Cr/Au electrodes 08 were deposited by electron beam evaporation. The device became a fully functional plasmon biosensor after the lift-off process. The sensor surface was covered with Su-8 2002 layer 09 except the sensing platform 10 which physically separated from two other Metal contacts. The Su-8 2002 layer 09 was deposited following the general development process. The fabricated sensors were characterized regarding their electrical performance before gold nanoparticles 04 were incorporated onto the sensing platform 10. Then, gold was patterned onto the sensing stage 10 using a photolithography method. Thereafter, thermal reflow method was employed to create self-assembled gold nanoparticles 04.

Several reflow conditions were tested to achieve a narrow size distribution and to optimize the semi-spherical shape of gold nanoparticles 04. The results were obtained with a 5 nm gold film treated at 250° C. for 10 minutes. The dimensions of the fabricated devices may be 100 μm×100 μm in channel length (L) and width (W), respectively. Also the sensing stage 10 where the gold nanoparticles 04 were assembled may be 50 μm×100 μm.

To fabricate microfluidic channel, the mold may be prepared using Su-8 2075. Below shows the method to tune the processing parameters on Si wafer <100> with regard to defining the recipe for the Su-8. At first, Su-8 2075 may be spin coated onto the biosensor, where the speed, ramp, and time of first time coating may be 500 RPM, 100 RPM/s, and 10 s, respectively, and the speed, ramp, and time of second time coating may be 1900 RPM, 300 RPM/s, and 30 s, respectively. Secondly, the coated biosensor may be pre-baked at 65° C. for 6 min and thereafter baked at 95° C. for 20 min. After cooling it down for 5 min, the biosensor may be exposed to 18.74 $mW/cm^2$ UV light for 32.02 s, and the required intensity may be 600 $mJ/cm^2$.

Thirdly, the biosensor may be pre-baked at 65° C. for 6 min, and thereafter baked at 95° C. for 10 min. After cooling it down to room temperature for 5 min, the biosensor may be developed in Su 8 developer for 6 min and rinsed by isopropanol and dried by $N_2$ gas. Finally, the biosensor may be baked at 105° C. for 5 min. The resultant developed Su-8 had 71 µm thickness. The thickness was measured using the step profiler. To obtain microfluidic channel, polydimethylsiloxane (PDMS) molding solution may be prepared by mixing Sylgard 184 Base with Curing Agent at a ratio of 10 (base, 25 g) to 1 (curing agent, 2.5 g) by weight for 15 mins. Then all bubbles may be removed from PDMS molding solution in Vacuum Chamber (Vacuum 25 psi for 15 mins twice). Thereafter the molding method followed as: a) put a patterned wafer in a petri dish; b) pour PDMS on the wafer; c) remove bubble again by using a pipette (without vacuum chamber); and d) put the Petri dish on an optical table, and wait for a day. After removing mold and cutting the patterned PDMS, PDMS microfluidic channel may be attached to the device.

Figure 11:
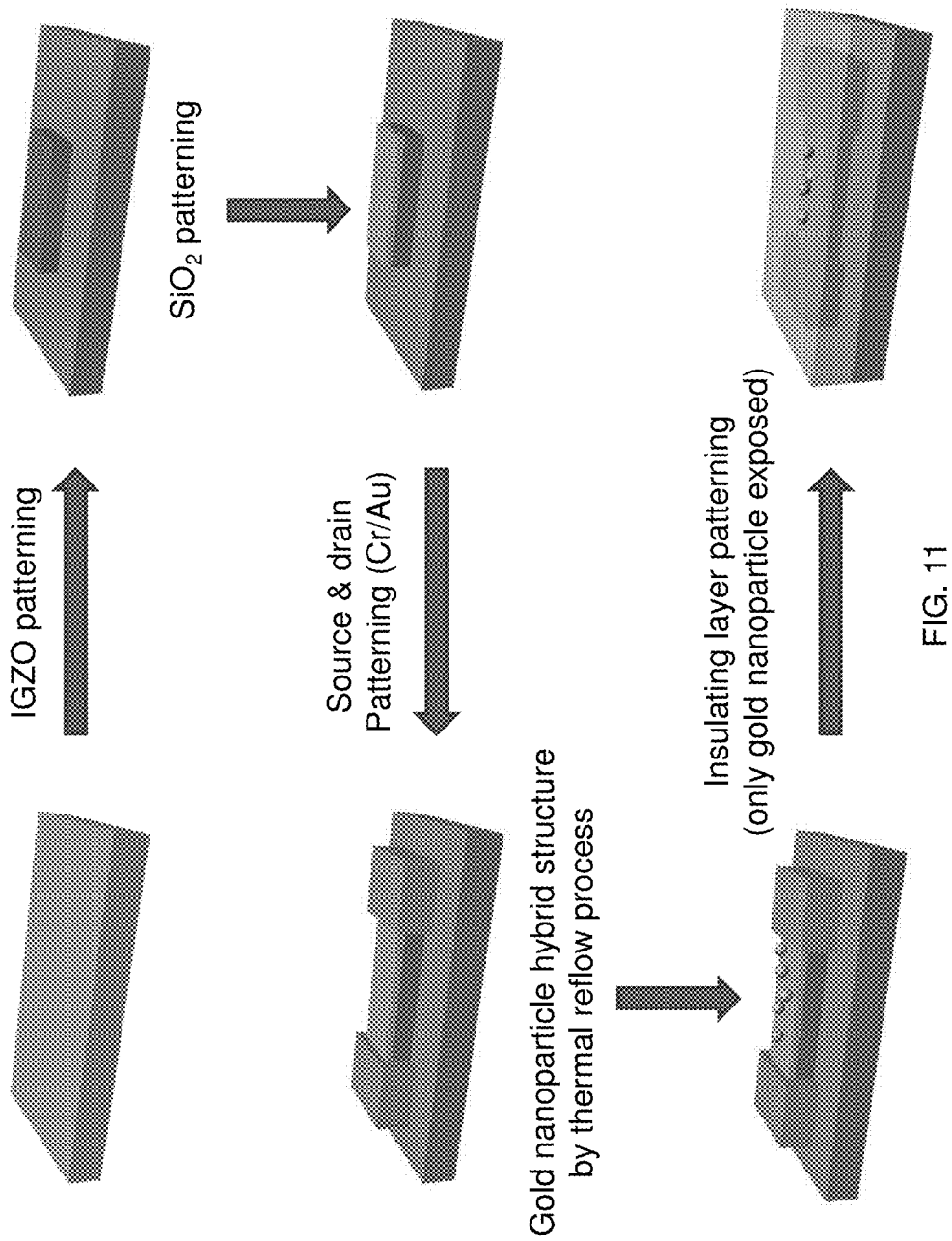
FIG. 11 is a fabrication flow diagram of the plasmonic photoconductor sensing platform.

FIG. 11 illustrates the fabrication process flow of the plasmonic photoconductor sensing platform. Similar to FIG. 10, IGZO may be patterned onto the silica insulating substrate 06 after typical photolithography process and HCl etching. Then $SiO_2$ film 05 may be patterned onto the IGZO film 03 using PECVD. Thereafter, the process may be the same as the fabrication process flow of FIG. 10.

Figure 12:
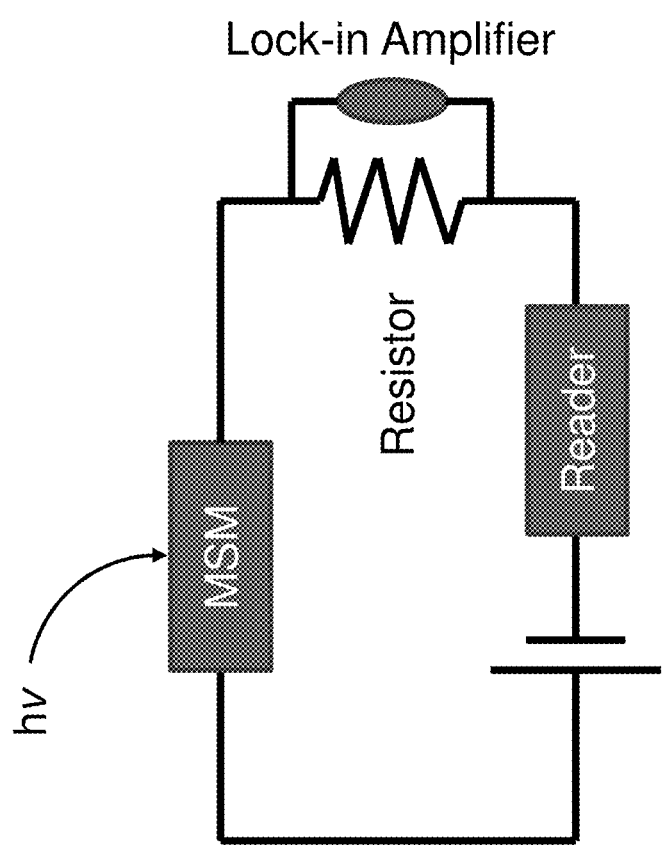
FIG. 12 is a schematic diagram of the portable biosensing system.

FIG. 12 illustrate the component of the portable biosensing system. One source meter may be employed to provide the voltage biases. Lock-in amplifier may be connected to the plasmonic photoconductor sensing platform to remove the background noise. The generated photocurrent from the plasmonic photoconductor sensing platform passed through a resistor so that the signal in the plasmonic photoconductor sensing platform has the voltage unit. The portable biosensing system may further include: at least one serial communication unit through USB; at least a signal processing software to read and analyze the sensor detection data; at least a host device such as the computer and the phone to demonstrate the result; at least one external light; and at least one narrowband optical filter at correspondence light emitting diode frequencies.

Figure 13:
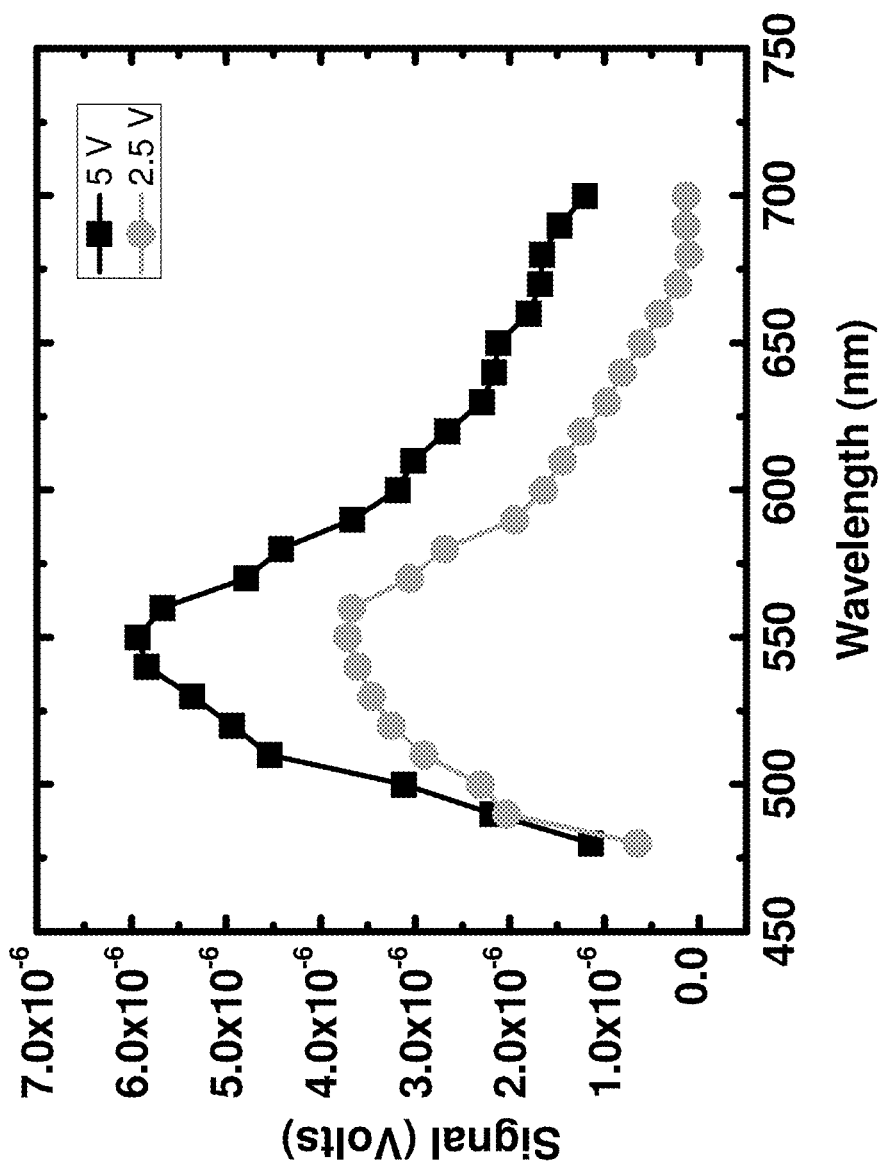
FIG. 13 is a diagram of the optical response of the portable biosensing system.

FIG. 13 illustrates electro-optical characterization of the portable biosensing system. One source meter (Keithley 2400) may be employed to provide the voltage biases for the electrical characterization of the plasmonic photoconductor sensing platform. The spectral response measurement may be carried out using a monochromatic light through a fiber-optic cable delivered on the sample with controlled angles at the probe station. The optical measurement system may be made up of a quartz tungsten halogen lamp (250 W, Oriel), a lock-in amplifier (SR830, Stanford Research) with a mechanical chopper, a monochromator (SP2300, Princeton Instruments), and appropriate optical filters to suppress the second harmonic lights from the monochromator. The light power was measured using a NIST calibrated silicon photodetector (FDS-1010CAL, Thorlabs) and an optical power meter (PM100D with S120VC, Thorlabs) for the spectral response calculation. The measured monochromatic optical power was controlled from 0.7 to 2 $mW/cm^2$ for the 400-800 nm spectral range. FIG. 13. presents the absorbance of gold nanoparticle 04 in the plasmonic photoconductor sensing platform 01 using 5 V and 2.5 V electric field.

Figure 14:
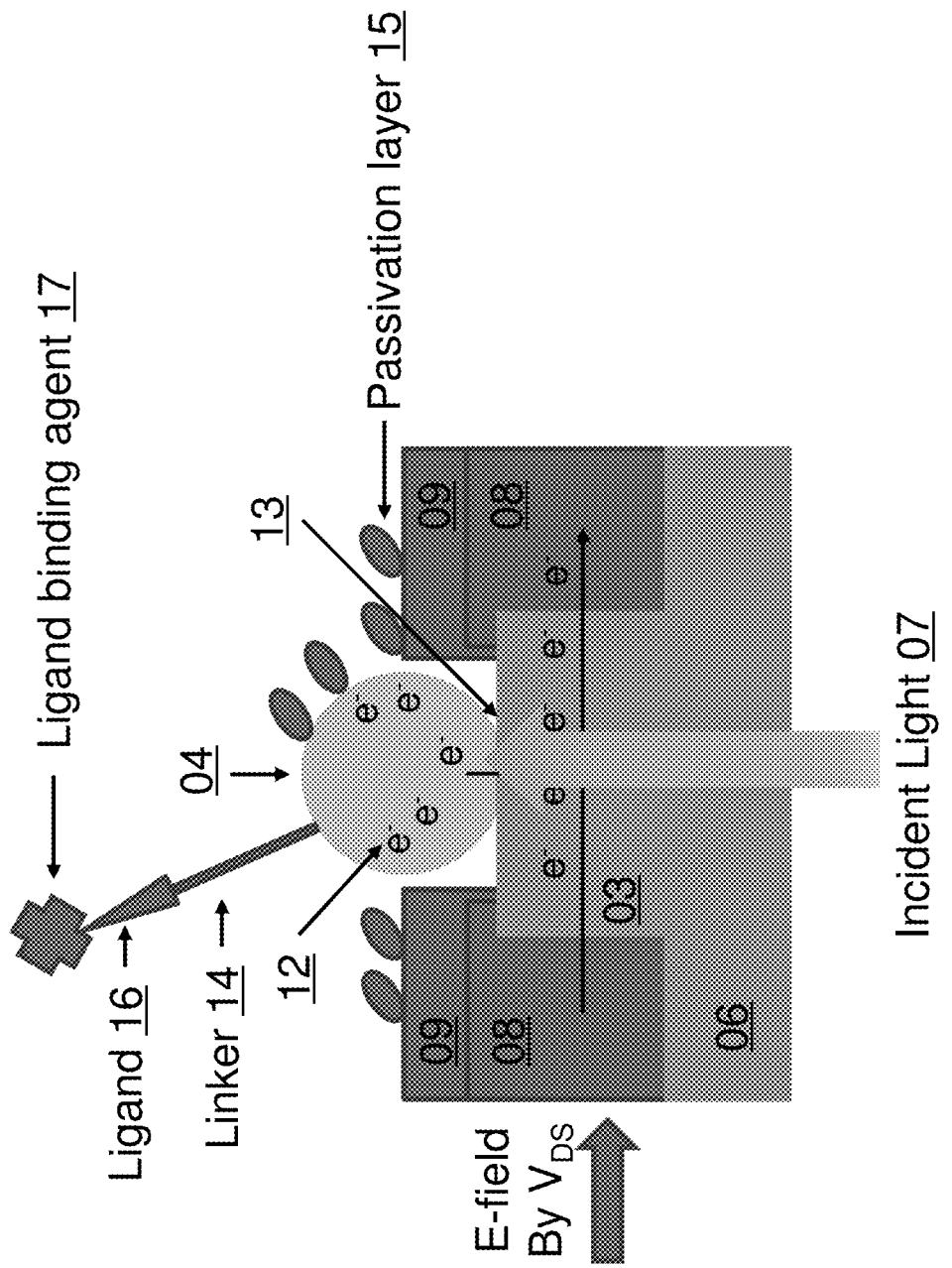
FIG. 14 is a diagram of the volume change of gold nanoparticle sensing area after functionalization.

FIG. 14 illustrates the functionalization of the plasmonic photoconductor sensing platform. All chemicals may be injected into the microfluidic channel 11 and delivered to the sensing stage 10 by a microfluidic kit. The ligand 16 may be attached to the plasmonic nanostructures 04 via a linker 14 which is not limited to oligopeptide linker or a hydrocarbon linker. The linker 14 molecule is one or more thiol groups terminated or disulfide groups terminated. The other end of the linker molecule may be, but is not limited to, N-hydroxysuccinamide (NHS) ester, aldehyde, maleimide, epoxide, a carboxyl group, an amine group, and a hydroxyl group.

After linker 14 functionalization, the unreacted linker 14 may be washed off by phosphate-buffered saline (PBS) buffer. Then ligand 16 will be delivered to the sensing platform 10 and incubated with the attached linker 14. The ligand 16 may be, but is not limited to, different biomarkers antibody, such as cardiac troponin I antibody. After incubation, unreacted ligand 16 may be washed off by phosphate-buffered saline (PBS) buffer. To eliminate non-specific binding, passivation layer 15 may then be delivered to the sensing platform 10. The passivation method includes one detergent blocker, such as Tween-20 and Triton X-100, and protein blockers, such as bovine serum albumin, casein, fish gelatin, and whole sera, and polymer based blockers, such as polyethylene glycol, polyvinyl alcohol, polyvinylpyrrolidone, polyacrylic acid, polyacrylic maleic acid.

In addition, if the linker 14 contains polyethylene glycol (PEG) moiety, it may also be one of the passivation methods. The ligand-binding agent 17 may be, but is not limited to, different biomarkers, such as cardiac troponin I and cardiac troponin T. After each molecule attachment, including linker 14 layer, ligand 16 layer, and the binding of ligand-binding agent 17 to the ligand 16 layer, the sensing volume of gold nanoparticle 04 may increase, which in turn may change the refractive index. This change may increase the absorption peak at the measured wavelength, which means the number of induced hot electrons will be larger.

Figure 15:
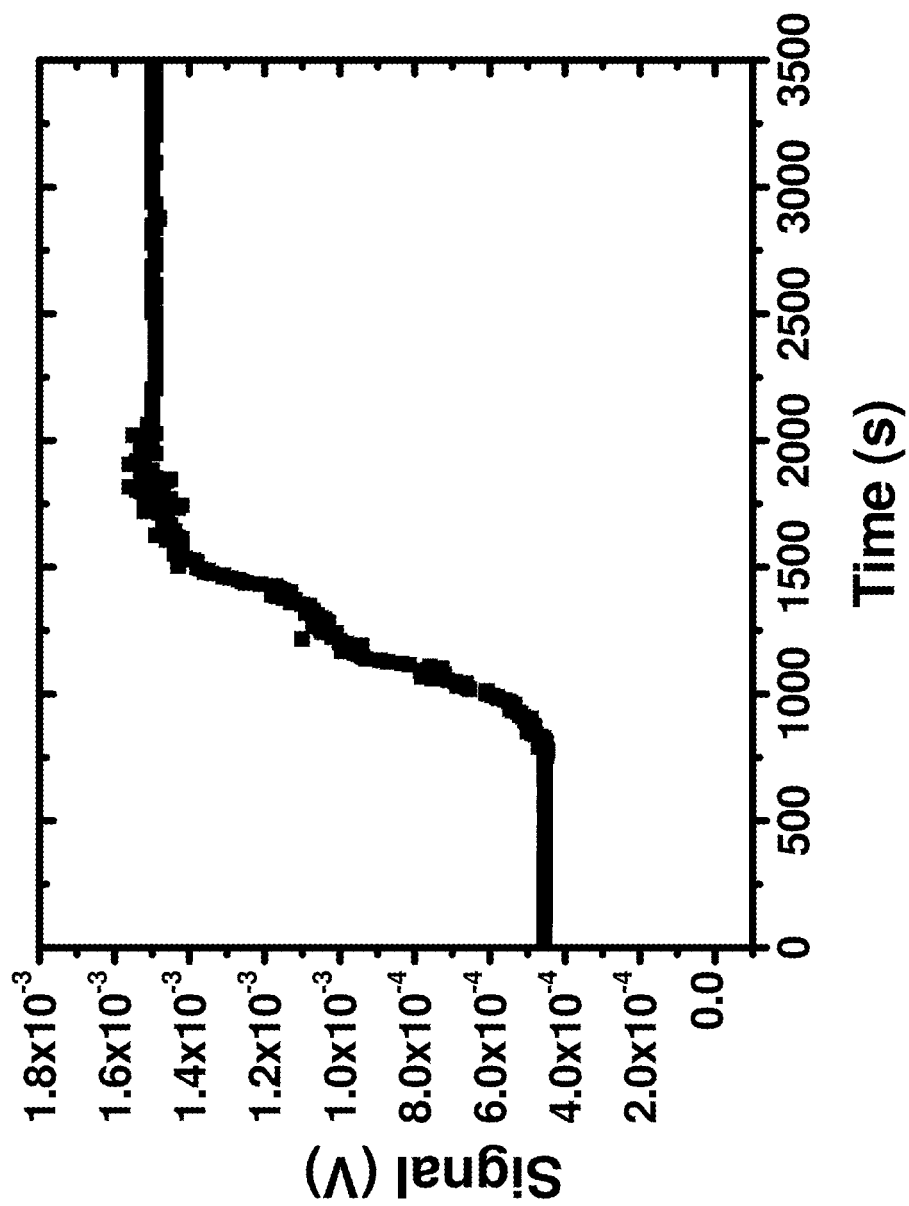
FIG. 15 is a diagram of one example of the real-time detection of cardiac troponin I.

FIG. 15 illustrates one example of the real-time detection of ligand binding agent 17 cardiac troponin I using the plasmonic sensing system 02. The linker 14 (1 mM 3-mercaptopropionic acid (MPA) ethanolic solution) may be injected into the microfluidic channel 11 to modify the gold nanoparticles 04 overnight. The ligand 16 human cardiac troponin I antibody may be conjugated onto the gold nanoparticles 04 via 1-ethyl-3-(-3-dimethylaminopropyl) carbodiimide hydrochloride (EDC) and N-hydroxysuccinimide (NHS) chemistry. After 1 hour incubation, passivation layer 15 (1% bovine serum albumin) may be added to block the non-specific binding site for 30 minutes. Ligand binding agent 17 cardiac troponin I (0.5 ng/mL) may be prepared in phosphate-buffered saline (PBS) buffer (pH=7.4). The absorbance intensity increases, and was recorded as a function of time, and the signal gets stabilized in approximately 1200 after the injection of the ligand binding agent 17, suggesting the accomplishment of the binding between the ligand 16 and ligand binding agent 17.

Figure 16:
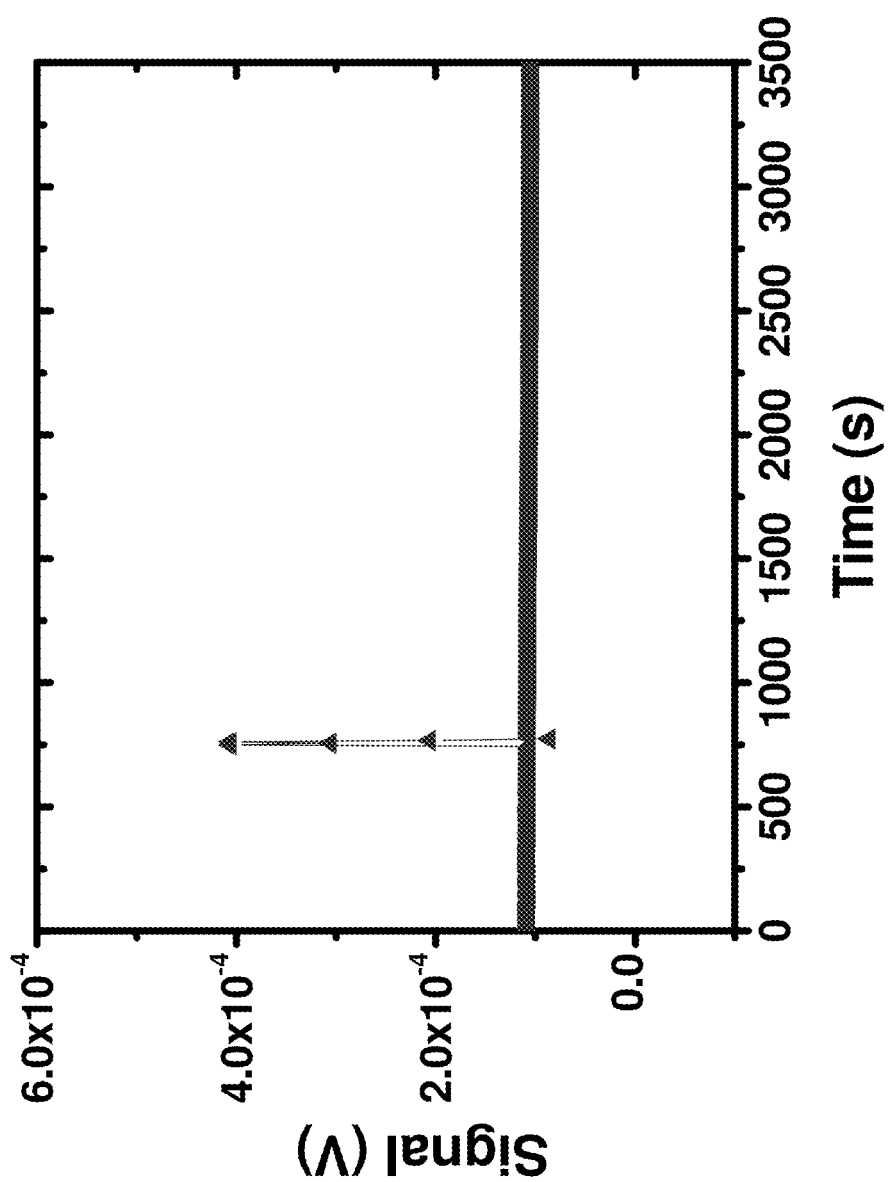
FIG. 16 is a diagram of one example of the real-time detection of cardiac troponin I using the portable biosensing system without gold nanoparticles 04.

FIG. 16 illustrates one example of the real-time detection of ligand binding agent 17 cardiac troponin I using the portable biosensing system without gold nanoparticles 04. Linker 14 and ligand 16 may be functionalized onto the IGZO film 03 surface following the same functionalizing method. The linker 14 (1 mM 3-mercaptopropionic acid (MPA) ethanolic solution) may be injected into the microfluidic channel 11 overnight. The ligand 16 human cardiac troponin I antibody were conjugated onto the gold nanoparticles 04 via 1-ethyl-3-(-3-dimethylaminopropyl) carbodiimide hydrochloride (EDC) and N-hydroxysuccinimide (NHS) chemistry. After 1 hour incubation, passivation layer 15 (1% bovine serum albumin) may be added to block the non-specific binding site for 30 minutes Ligand binding agent 17 cardiac troponin I (0.5 ng/mL) may be prepared in phosphate-buffered saline (PBS) buffer (pH=7.4). Gold nanoparticles 04 may be the key to the whole detection mechanism. Therefore, missing gold nanoparticles 04 or the physiological absorption of ligand binding agent 17 to the detection platform surface, present no results with regard to the detection of ligand binding agent 17.

Figure 17:
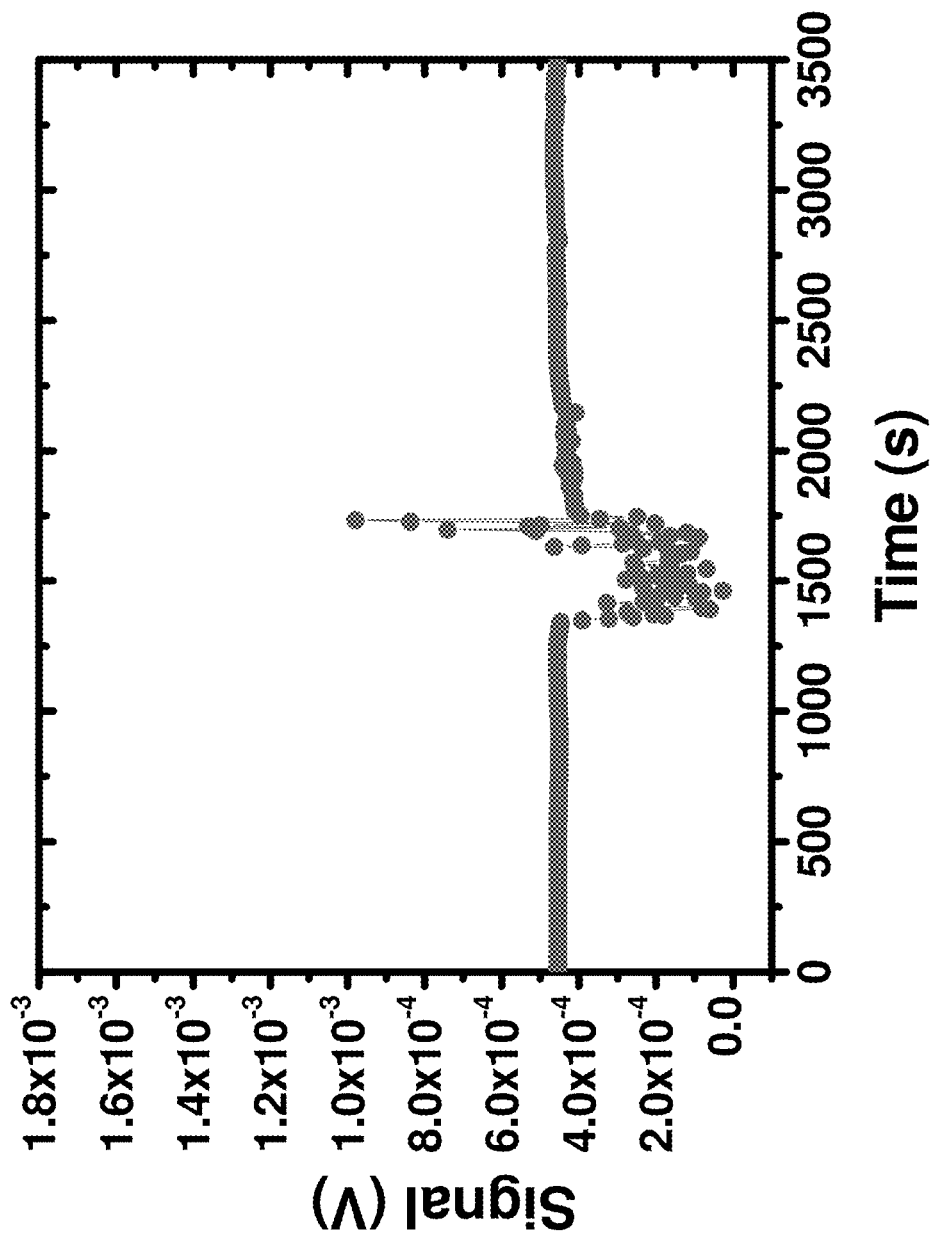
FIG. 17 is a diagram of one example of the real-time detection of insulin using the portable biosensing system.

FIG. 17 illustrates one example of the real-time detection of ligand binding agent 17 insulin using the portable biosensing system. The linker 14 (1 mM 3-mercaptopropionic acid (MPA) ethanolic solution) may be injected into the microfluidic channel 11 to modify the gold nanoparticles 04 overnight. The ligand 16 human cardiac troponin I antibody may be conjugated onto the gold nanoparticles 04 via 1-ethyl-3-(-3-dimethylaminopropyl) carbodiimide hydrochloride (EDC) and N-hydroxysuccinimide (NHS) chemistry. After 1 hour incubation, passivation layer 15 (1% bovine serum albumin) may be added to block the non-specific binding site for 30 minutes Ligand binding agent 17 insulin (1 mg/mL) may be prepared in phosphate-buffered saline (PBS) buffer (pH=7.4). The portable biosensing is functionalized with the ligand 16 cardiac troponin I antibody. No significant bindings may be observed in the detection window due to no binding of ligand 16 to ligand binding agent 17 insulin, which in turn confirms the specificity of the portable biosensing.

Figure 18:
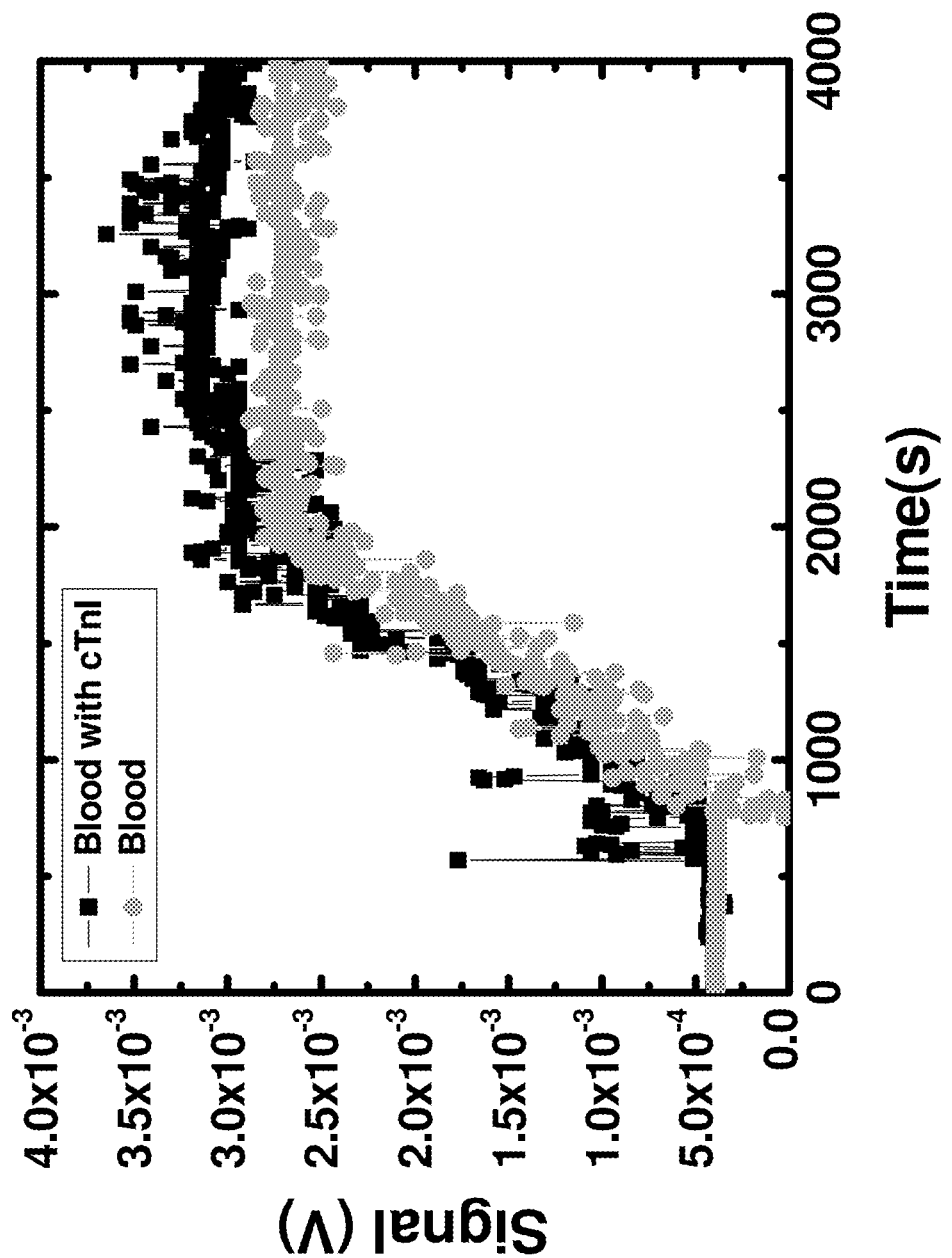
FIG. 18 is a diagram of one example of the real-time detection of cardiac troponin I using the portable biosensing system.
Figure 19:
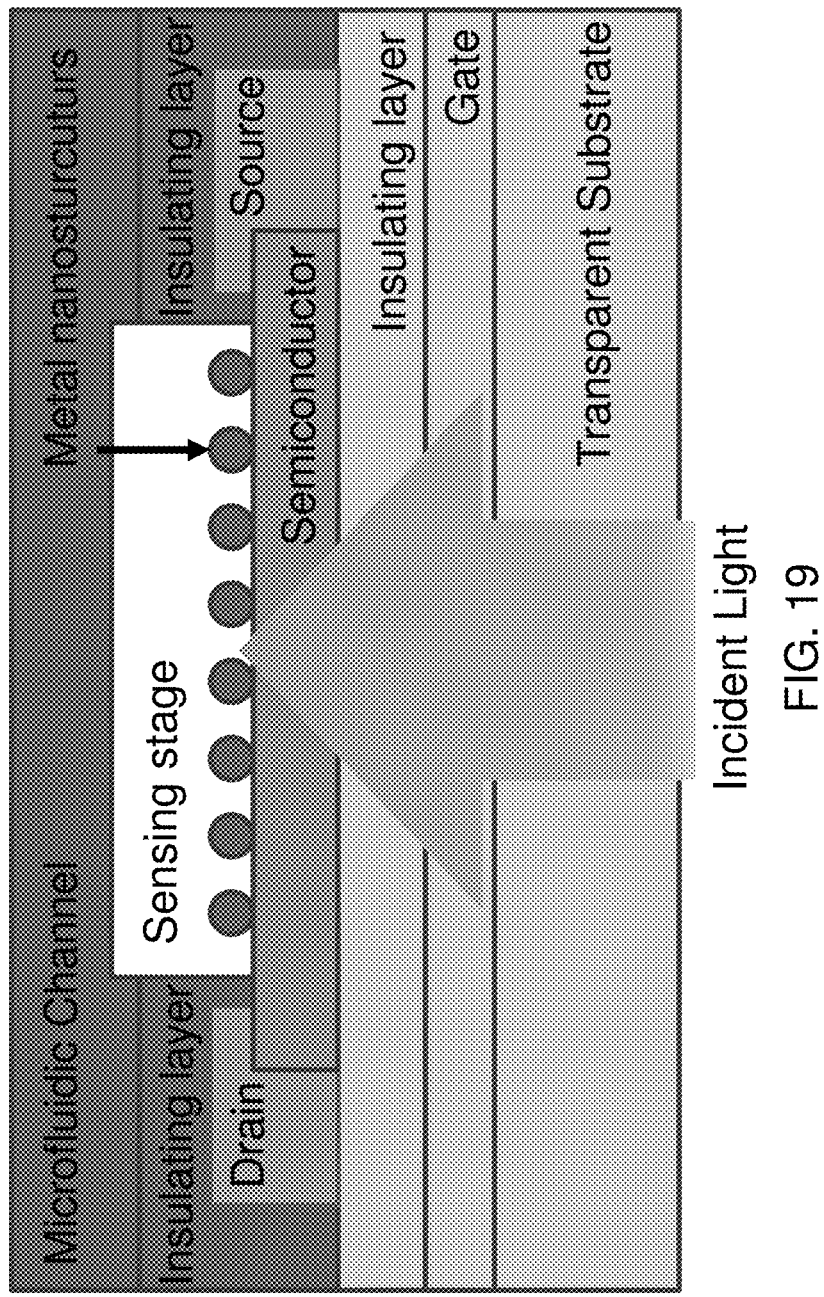
FIG. 19 is a diagram of the structure of the plasmon field effect transistor.

FIG. 18 illustrates one example of the real-time detection of ligand binding agent 17 cardiac troponin I using the portable biosensing system. The linker 14 (1 mM 3-mercaptopropionic acid (MPA) ethanolic solution) may be injected into the microfluidic channel 11 to modify the gold nanoparticles 04 overnight. The ligand 16 human cardiac troponin I antibody may be conjugated onto the gold nanoparticles 04 via 1-ethyl-3-(-3-dimethylaminopropyl) carbodiimide hydrochloride (EDC) and N-hydroxysuccinimide (NHS) chemistry. After 1 hour incubation, passivation layer 15 (1% bovine serum albumin) may be added to block the non-specific binding site for 30 minutes. Ligand binding agent 17 cardiac troponin I (0.1 ng/mL) may be prepared in whole human blood. Blood with and without ligand binding agent 17 cardiac troponin I (0.1 ng/mL) may be injected into the portable biosensing system, respectively. The signal difference represents the detection of ligand binding agent 17 cardiac troponin I.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A plasmonic photoconductor sensing platform, comprising:
    an insulating substrate;
    a semiconducting film placed on top of the insulating substrate;
    two metal contacts placed at least in part on the semiconducting film to enforce an electric field;
    a plurality of plasmonic nanostructures deposited on the semiconducting film and physically separated from metal contacts;
    an insulating layer physical separate from the plurality of plasmonic nanostructures, the insulating layer electrically isolating the plasmonic nanostructures from the two metal contacts;
    at least one energy source; and
    at least one microfluidic channel disposed on the insulating layer.

2. The plasmonic photoconductor sensing platform of claim 1, wherein the semiconducting film provides an electron path.

3. The plasmonic photoconductor sensing platform of claim 1, wherein the plurality of plasmonic nanostructures are configured to:
    absorb photons provided by a light source; and
    generate plasmonic hot electrons to affect a photocurrent in the semiconducting film.

4. The plasmonic photoconductor sensing platform of claim 1, wherein the plurality of plasmonic nanostructures and the semiconducting film create a Schottky Junction that allows only plasmonic hot electron transfer from the plurality of plasmonic nanostructures to the semiconducting film.

5. The plasmonic photoconductor sensing platform of claim 1, wherein a light source provides back side illumination, and is placed at least one of below the insulating substrate, partially or fully embedded inside the insulating substrate, and on top of the insulating substrate.

6. The plasmonic photoconductor sensing platform of claim 1, wherein a light source is modulated with a narrow optical or polarizer filer or a switching electric circuit to provide energy with a different wavelength number.

7. The plasmonic photoconductor sensing platform of claim 1, wherein an inlet of the microfluidic channel includes at least one plasma separation membrane that is aligned to the plasmonic photoconductor sensing platform such that the plurality of plasmonic nanostructures are in direct contact with the microfluidic channel.

8. The plasmonic photoconductor sensing platform of claim 1, further comprising an insulating wall between the semiconducting film and the plurality of plasmonic nanostructures.

9. The plasmonic photoconductor sensing platform of claim 8, wherein the semiconducting film and plurality of plasmonic nanostructures are in direct contact with the insulating wall.

10. The plasmonic photoconductor sensing platform of claim 8, wherein the insulating wall is one of $SiO_2$ and HfO.

11. The plasmonic photoconductor sensing platform of claim 8, wherein a light source is located at one of below the insulating wall, partially or fully embedded inside the insulating wall, and on top of the insulating wall.

12. The plasmonic photoconductor sensing platform of claim 1, wherein the insulating substrate is transparent in or opaque in visible spectrum; and
    the semiconducting film has an absorption spectrum that does not overlap with a plasmonic resonance spectrum.

13. The plasmonic photoconductor sensing platform of claim 1, further comprising metal contacts for voltage bias.

14. The plasmonic photoconductor sensing platform of claim 1, wherein the plurality of plasmonic nanostructures are at least one of gold, silver, aluminum, copper, tungsten and doped metal oxide; and
    a shape of the plurality of plasmonic nanostructures is at least one of sphere, semi-sphere, cylinder, cube, cone, pyramid or other geometric structure.

15. The plasmonic photoconductor sensing platform of claim 1, wherein the microfluidic channel is at least one of polydimethylsiloxane (PDMS) molding solution, polyethylene terephthalate (PET), and poly(methyl methacrylate) (PMMA).

16. The plasmonic photoconductor sensing platform of claim 1, wherein the at least one microfluidic channel is disposed directly on the insulating layer.

* * * * *